(12) United States Patent
Hiroshima et al.

(10) Patent No.: US 10,568,581 B2
(45) Date of Patent: Feb. 25, 2020

(54) PULSIMETER, FREQUENCY ANALYSIS DEVICE, AND PULSE MEASUREMENT METHOD

(71) Applicant: Renesas Electronics Corporation, Tokyo (JP)

(72) Inventors: Akane Hiroshima, Tokyo (JP); Naoya Tokimoto, Tokyo (JP); Yuji Shimizu, Tokyo (JP)

(73) Assignee: RENESAS ELECTRONICS CORPORATION, Tokyo (JP)

( * ) Notice: Subject to any disclaimer, the term of this patent is extended or adjusted under 35 U.S.C. 154(b) by 1110 days.

(21) Appl. No.: 14/956,593

(22) Filed: Dec. 2, 2015

(65) Prior Publication Data
US 2016/0235371 A1 Aug. 18, 2016

(30) Foreign Application Priority Data
Feb. 12, 2015 (JP) .................................. 2015-025253

(51) Int. Cl.
*A61B 5/00* (2006.01)
*A61B 5/024* (2006.01)
*G06F 19/00* (2018.01)

(52) U.S. Cl.
CPC ........ *A61B 5/7257* (2013.01); *A61B 5/02416* (2013.01); *A61B 5/6826* (2013.01); *A61B 5/7225* (2013.01); *A61B 5/7278* (2013.01); *G06F 19/3481* (2013.01)

(58) Field of Classification Search
CPC . A61B 5/7257; A61B 5/6826; A61B 5/02416; A61B 5/7225; A61B 5/7278; G06F 19/3481
See application file for complete search history.

(56) References Cited

U.S. PATENT DOCUMENTS

| 5,924,980 A * | 7/1999 | Coetzee ............. A61B 5/14551 128/901 |
| 2011/0055306 A1* | 3/2011 | Dean ..................... G06F 17/141 708/401 |

FOREIGN PATENT DOCUMENTS

JP          10-258039 A          9/1998

OTHER PUBLICATIONS

Taiwanese Office Action issued in corresponding Taiwanese Patent Application No. 104138776, dated Jun. 3, 2019, with English Translation.

* cited by examiner

*Primary Examiner* — Peter Luong
(74) *Attorney, Agent, or Firm* — McDermott Will & Emery LLP

(57) ABSTRACT

An object of the invention is to shorten a measurement time while preventing deterioration in resolution during frequency analysis and preventing a reduction in measurement range. A pulsimeter (1) includes a pulse data acquisition unit (100), a replication unit (16), and a frequency analysis unit (17). The replication unit (16) generates, when the number of pieces of acquired sampling data for a pulse rate calculation reaches n, m pieces of sampling data using the n pieces of sampling data and data obtained by replicating n-th sampling data. The frequency analysis unit (17) performs a frequency analysis on the m pieces of sampling data.

15 Claims, 12 Drawing Sheets

PULSIMETER, FREQUENCY ANALYSIS DEVICE, AND PULSE MEASUREMENT METHOD

CROSS-REFERENCE TO RELATED APPLICATIONS

This application is based upon and claims the benefit of priority from Japanese patent application No. 2015-025253, filed on Feb. 12, 2015, the disclosure of which is incorporated herein in its entirety by reference.

BACKGROUND

The present invention relates to a pulsimeter, a frequency analysis device, and a pulse measurement method. For example, the present invention relates to a pulsimeter, a frequency analysis device, and a pulse measurement method which perform a frequency analysis.

A pulsimeter configured using a pulse sensor including a light emitting device, such as an LED (light emitting diode), and a photodetector, such as a phototransistor or a photodiode, is known. As a method of obtaining a pulse rate from an output of the pulse sensor, there is a method in which a frequency analysis is performed by performing Fourier transform processing on the output from the sensor and a pulse rate is calculated based on the analysis result.

Due to the nature of the Fourier transform processing that calculates frequency components of input data, the Fourier transform processing requires an approximate number of pieces of input data, i.e., an approximate number of samples. The number of pieces of input data depends on a measurement time. In order to calculate a pulse rate with a high resolution and extend the upper limit of a measurement range, it is necessary to increase the number of pieces of input data. Accordingly, when the Fourier transform processing is performed on a predetermined sample number of data sequences so as to satisfy the performance required by a system, the Fourier transform processing cannot be performed until a necessary number of pieces of input data are obtained, so that it takes a long time to output the pulse rate.

On the other hand, Japanese Unexamined Patent Application Publication No. H10-258039 discloses a technique in which in fast Fourier transform (FFT) processing using 128 pieces of sampling data as a processing unit, the FFT processing is performed on 128 pieces of latest pulse wave data every time 32 pieces of pulse wave data are acquired, thereby shortening the time required for outputting the result.

SUMMARY

In the technique disclosed in Japanese Unexamined Patent Application Publication No. H10-258039, if the number of pieces of acquired sampling data is less than 128, data is supplemented with "0" data as data indicating the center value of the pulse wave data, thereby obtaining 128 pieces of sampling data.

However, there is a problem that when data is supplemented with "0" data so as to obtain the necessary number of pieces of data as the processing unit of the FFT, it may be difficult to acquire the correct pulse rate due to the effect of signal components other than the pulse wave that are included in the pulse wave data.

Other problems to be solved by and novel features of the present invention will become apparent from the following description and the accompanying drawings.

A first aspect of the present invention is a pulsimeter including: a replication unit that generates, when the number of pieces of acquired sampling data reaches n (n is a positive integer), m (m is a positive integer, and m>n) pieces of sampling data using the n pieces of sampling data and data obtained by replicating n-th sampling data; and a frequency analysis unit that performs a frequency analysis on the m pieces of sampling data.

According to the first aspect of the invention, it is possible to shorten a measurement time while preventing deterioration in resolution during frequency analysis and preventing a reduction in measurement range.

BRIEF DESCRIPTION OF THE DRAWINGS

The above and other aspects, advantages and features will be more apparent from the following description of certain embodiments taken in conjunction with the accompanying drawings, in which.

DETAILED DESCRIPTION

Figure 1:
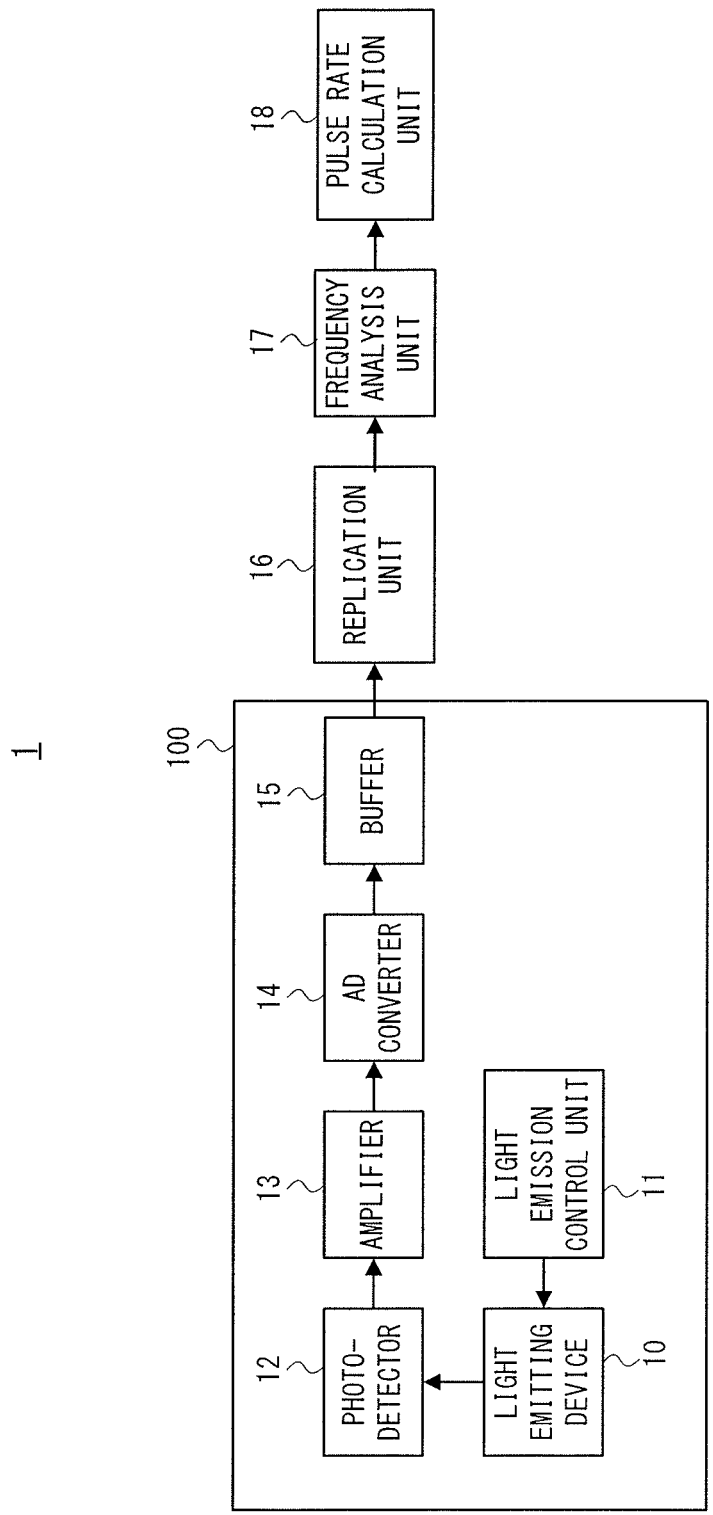
FIG. 1 is a block diagram showing a configuration of a pulsimeter according to a first embodiment.

The following description and the drawings are abbreviated and simplified as appropriate for clarity of explanation. The elements illustrated in the drawings as functional blocks for performing various processes may be implemented hardwarewise by a CPU, a memory, and other circuits, and softwarewise by a program loaded into a memory or the like. Accordingly, it is understood by those skilled in the art that the functional blocks may be achieved in various forms including hardware alone, software alone, and combinations thereof, and not limited to any of them. Note that in the drawings, the same elements are denoted by the same reference numerals, and repeated explanations are omitted as appropriate.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (Read Only Memory), CD-R, CD-R/W, and semiconductor memories (such as mask ROM, PROM (programmable ROM), EPROM (erasable PROM), flash ROM, RAM (Random Access Memory), etc.). The program may be provided to a computer using any type of transitory computer readable media. Examples of transitory computer readable media include electric signals, optical signals, and electromagnetic waves. Transitory computer readable media can provide the program to a computer via a wired communication line, such as electric wires and optical fibers, or a wireless communication line.

First Embodiment

FIG. 1 is a block diagram showing a configuration of a pulsimeter 1 according to a first embodiment. The pulsimeter 1 includes a pulse data acquisition unit 100, a replication unit 16, a frequency analysis unit 17, and a pulse rate calculation unit 18. The pulse data acquisition unit 100 may have any configuration as long as it can sequentially acquire sampling data for a pulse rate calculation. In the first embodiment, the pulse data acquisition unit 100 is implemented by a configuration including a light emitting device 10, a light emission control unit 11, a photodetector 12, an amplifier 13, an AD converter 14, and a buffer 15.

The light emitting device 10 is, for example, an LED, and emits light under the control of the light emission control unit 11. In the case of measuring a pulse, the light emitting device 10 emits light to blood vessels of a person to be measured. The light emitting device 10 may include one or more LEDs. As the light to be emitted from the light emitting device 10, light of any color, such as green, red, and infrared light, can be used. The light emission control unit 11 controls the timing of light emission of the light emitting device 10. The light emission control unit 11 transmits, to the light emitting device 10, a control signal to perform an operation, such as continuous light emission, or repetition of turning on and off in a predetermined period. The light emission control unit 11 may control the amount of luminescence of the light emitting device 10. In this case, for example, the light emission control unit 11 may control the amount of luminescence according to the strength of a signal detected by the photodetector 12.

Figure 2:
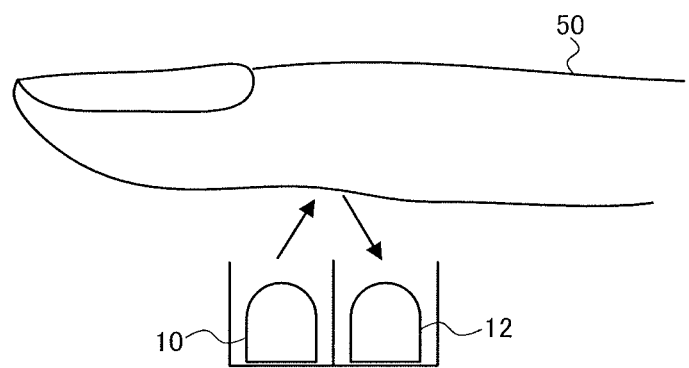
FIG. 2 is a schematic diagram showing a state in which pulse data is acquired by a light emitting device and a photodetector.

The photodetector 12 is configured using, for example, a phototransistor or a photodiode. In the case of measuring a pulse, the photodetector 12 detects light from the light emitting device 10 through blood vessels of a person to be measured. In the first embodiment, as shown in FIG. 2, the light emitting device 10 and the photodetector 12 are arranged in the same direction with respect to a part of a human body to be measured (a finger 50 in the example shown in FIG. 2). Accordingly, the photodetector 12 detects reflected light which is emitted from the light emitting device 10 and reflected by the part of the human body to be measured. More specifically, the photodetector 12 detects the light from the light emitting device 10 that is reflected from the blood vessels of the person to be measured. The part of the human body to be irradiated with light by the light emitting device 10 is not limited to a finger. Examples of a part of the human body may include an arm. In this manner, when a reflection sensor is used, there is no need to arrange the light emitting device and the photodetector so as to be opposed to each other with the part of the human body interposed therebetween. This contributes to miniaturization of the device. The first embodiment adopts the configuration in which the pulse of the provided human body is measured by irradiating the part of the human body with light, which leads to a reduction of the load on the person to be measured.

The intensity of light detected by the photodetector 12 varies in accordance with the pulsation of blood vessels. The pulsimeter 1 calculates the pulse rate as described below by obtaining the variations in the intensity of light.

The amplifier 13 is composed of, for example, an amplifier, and amplifies a signal detected by the photodetector 12. The amplifier 13 may be a programmable instrumentation amplifier capable of changing a gain, or a current-to-voltage conversion amplifier. However, when the output from the photodetector 12 is sufficient, it is not necessary to provide the amplifier 13.

The AD converter 14 performs an analog-to-digital conversion of the signal, which is amplified by the amplifier 13, with a predetermined sampling period. This allows an analog signal output from the amplifier 13 to be converted into digital data which is sampling data for a pulse rate calculation. Since the light emission of the light emitting device 10 is repeated after the measurement is started, the AD converter 14 sequentially outputs the sampling data.

The buffer 15 is, for example, a storage unit, such as a memory, and temporarily stores the sampling data output from the AD converter 14.

In the case of performing a frequency analysis, a predetermined number of pieces of sampling data are required. For example, in the case of Fourier transform, the number of samples required for the analysis is determined by a measurement range and a resolution which are required as specifications for the pulsimeter 1. The term "resolution" used herein refers to a resolution of a frequency to be analyzed, i.e., a pulse rate. The term "measurement range" used herein refers to a range of measurable frequencies, i.e., a range of measurable pulse rates. In the case of Fourier transform, as the number of pieces of sampling data increases, the resolution and the measurement range increase. On the other hand, as the number of pieces of sampling data decreases, the resolution and the measurement range decrease. Accordingly, a predetermined number of pieces of sampling data determined by the resolution, the measurement range, and the like, which are required as specifications for the pulsimeter 1, are necessary for the frequency analysis. In the following description, the predetermined number of samples determined by the resolution, the measurement range, and the like, which are required as specifications for the pulsimeter 1, are also referred to as a required sample number.

In the case of measuring a pulse rate during exercise or walking, for example, by using a smart watch, a fitness machine, or a lifelogging device, there is a possibility that variations in the pulse cannot be measured. For this reason, it is necessary to shorten a measurement time. Accordingly, there is a need for performing a frequency analysis in a short period of time, instead of performing a frequency analysis at time intervals in which the required number of pieces of sampling data are acquired. To achieve this without sacrificing the resolution and the measurement range, sampling data is replicated in the first embodiment so that the number of pieces of data reaches the required sample number.

Figure 3:
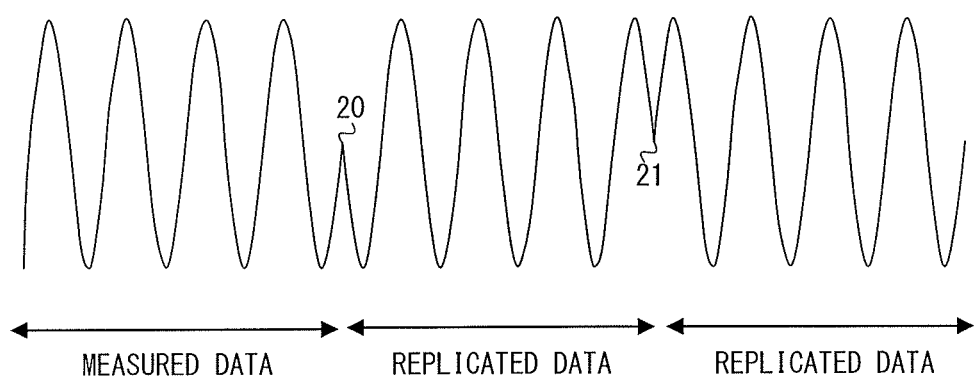
FIG. 3 is a graph showing an example of a data sequence generated by replicating a sampling data sequence actually measured.

In this case, as a method of complimenting data using replicated data so that the number of pieces of data used for frequency analysis processing reaches the required sample number, as shown in FIG. 3, replicated data sequences obtained by replicating a plurality of sampling data sequences actually measured can be arranged after the sampling data sequence to be replicated. However, when the data is supplemented in this manner, distortion occurs at joint portions 20 and 21 of the data sequences, so that the frequency of the signal is modulated. As a result, a frequency component generated due to the distortion caused by the replication of data may be erroneously detected as a frequency of the pulse.

The replication unit 16 replicates data in the manner as described below.

When the number of pieces of sampling data stored in the buffer 15 reaches a certain number, the replication unit 16 extracts data and replicates the extracted data. Specifically, the replication unit 16 replicates only the predetermined second data number of pieces of last obtained sampling data among the predetermined first data number of pieces of sampling data sequentially obtained. More specifically, when the number of pieces of obtained sampling data reaches n (n is a positive integer), the replication unit 16 generates m (m is a positive integer, and m>n) pieces of sampling data using the n pieces of sampling data and data obtained by replicating the n-th sampling data. Note that the first data number may be the same as the second data number, or the first data number may be larger than the second data number. The second data number may be larger than the first data number. In this case, however, the sum of the first data number and the second data number is equal to the required sample number.

Further, the replication unit 16 inserts the second data number of pieces of replicated data after the first data number of pieces of sampling data, and outputs a data sequence including the required sample number of pieces of data to the frequency analysis unit 17. Every time the number of pieces of sampling data newly stored in the buffer 15 reaches the first data number, the replication unit 16 performs the above-mentioned replication process on the first data number of pieces of sampling data newly stored, and outputs a data sequence including the required sample number of pieces of data to the frequency analysis unit 17.

The frequency analysis unit 17 performs a frequency analysis on the required sample number of the data sequences output from the replication unit 16. Specifically, the frequency analysis unit 17 performs the frequency analysis on the m pieces of sampling data. More specifically, the frequency analysis unit 17 performs FFT processing.

Specifically, when the first data number of pieces of sampling data is acquired after the pulse measurement is started, the frequency analysis unit 17 performs a first frequency analysis. After the first data number of pieces of sampling data are acquired once, every time the first data number of pieces of sampling data are acquired, the frequency analysis unit 17 performs a frequency analysis on the data sequence in which the first data number of pieces of latest sampling data are followed by data obtained by replicating the second data number of pieces of last obtained sampling data among the first data number of pieces of latest sampling data. Specifically, every time the pulse data acquisition unit 100 acquires the n pieces of sampling data, the replication unit 16 generates m pieces of sampling data and the frequency analysis unit 17 performs the frequency analysis on the m pieces of sampling data. Note that operations of the replication unit 16 and the frequency analysis unit 17 according to the first embodiment will be described later with reference to FIG. 4 based on specific examples.

The pulse rate calculation unit 18 calculates a pulse rate based on the result of the analysis by the frequency analysis unit 17. Specifically, the pulse rate calculation unit 18 extracts, from the frequency components analyzed by the frequency analysis unit 17, a frequency having a maximum spectrum value as a frequency corresponding to a pulse, and calculates the pulse rate based on the extracted frequency. The pulse rate is calculated by converting the extracted frequency into the frequency of pulses per minute. The pulse rate calculation unit 18 outputs the calculated pulse rate. For example, the pulse rate calculation unit 18 may display and output the pulse rate to a display unit such as a display which is not shown.

Figure 4:
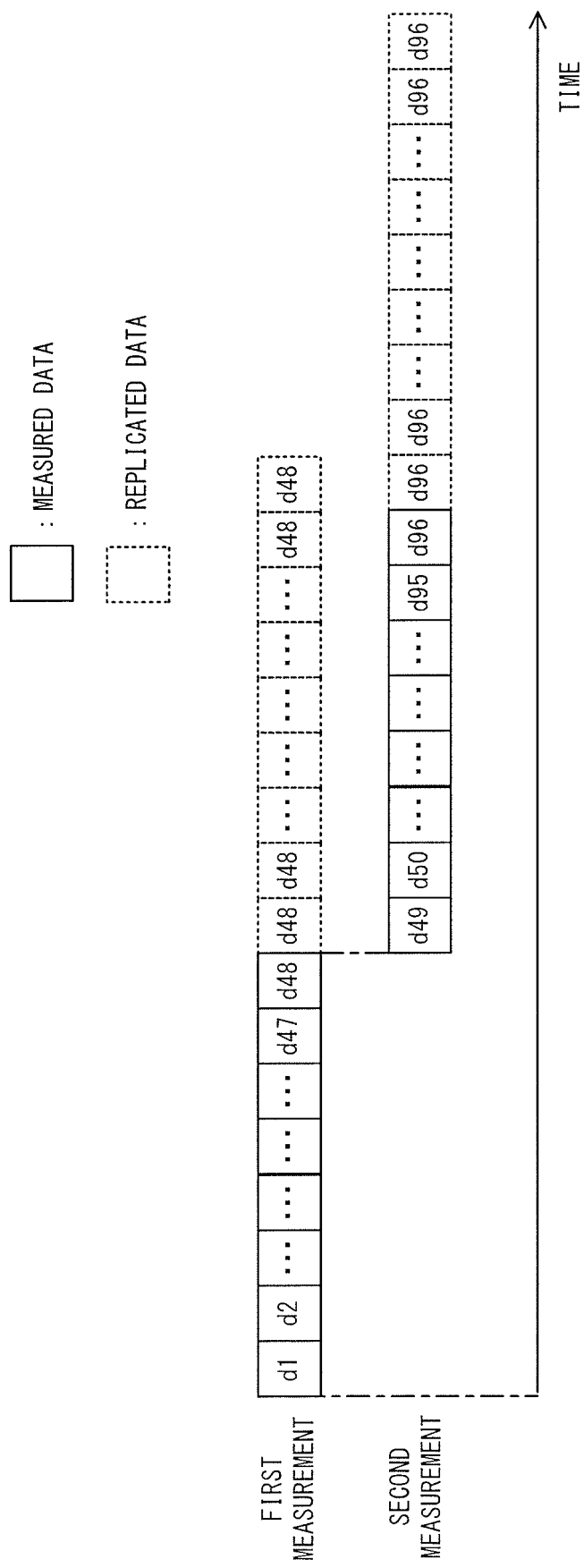
FIG. 4 is a schematic diagram illustrating a flow of operation of the pulsimeter according to the first embodiment.

The operation of the pulsimeter 1 will be described below with reference to FIG. 4. In an example shown in FIG. 4, assume that the required sample number is 128; the first data number indicating the number of pieces of actually measured sampling data is 48; and the second data number indicating the number of pieces of replicated data supplemented to secure the required sample number is 80. Note that these numbers are merely examples and are not particularly limited. In FIG. 4, each rectangle indicated by a solid line represents actually measured sampling data and each rectangle indicated by a broken line represents replicated sampling data.

In this specific example, when the measurement is started and 48 pieces of sampling data are acquired, a first pulse rate measurement is carried out. In other words, when 48 pieces of sampling data are acquired, a first output of the pulse rate is obtained. Further, when 48 pieces of sampling data are acquired, a second pulse rate measurement is carried out. More specifically, with the lapse of time from the start of the measurement, sampling data d1, sampling data d2, and . . . are sequentially accumulated in the buffer 15. When the 48th sampling data d48 counted from the start of the measurement is accumulated in the buffer 15, the replication unit 16 replicates 80 pieces of the sampling data d48. Upon completion of the replication, the replication unit 16 instructs the frequency analysis unit 17 to start the frequency analysis processing. Accordingly, the frequency analysis unit 17 performs the frequency analysis on 128 data sequences in which 48 data sequences from the sampling data d1 to the sampling data d48 are followed by 80 pieces of the sampling data d48. Through this process, the pulse rate is obtained before the number of pieces of sampling data acquired by the actual measurement reaches the required sample number.

Further, with the lapse of time from the start of the measurement, when the 96th sampling data d96 counted from the start of the measurement is accumulated in the buffer 15, the replication unit 16 replicates 80 pieces of the sampling data d96. The frequency analysis unit 17 performs the frequency analysis on 128 data sequences in which 48 data sequences from the 49th sampling data d49 counted from the start of the measurement to the 96th sampling data d96 counted from the start of the measurement are followed by 80 pieces of the sampling data d96. Thus, according to the pulsimeter 1, the pulse rate is obtained every time the first data number of pieces (48 pieces in this example) of sampling data are acquired.

Next, advantageous effects of the pulsimeter 1 according to this embodiment will be described with reference to a comparative example. In the comparative example, assume that the frequency analysis is performed by supplementing a shortage of data with "0" data.

The sampling data obtained by detecting the light emitted to apart of a human body includes not only signal components associated with the pulse, but also signal components obtained by the reflection of light (reflection of light on skin, a bone, or the like) other than those associated with the pulse. When a reflection sensor as shown in FIG. 2 is used, the contamination of other signal components is more significant than when a transmission sensor that receives light, which has been transmitted through a finger, on a side opposite to a light emission side is used. The other signal components have a value larger than that of the signal components associated with the pulse. Thus, the other signal components can be regarded as DC offset signals with respect to the signal components associated with the pulse.

Figure 5:
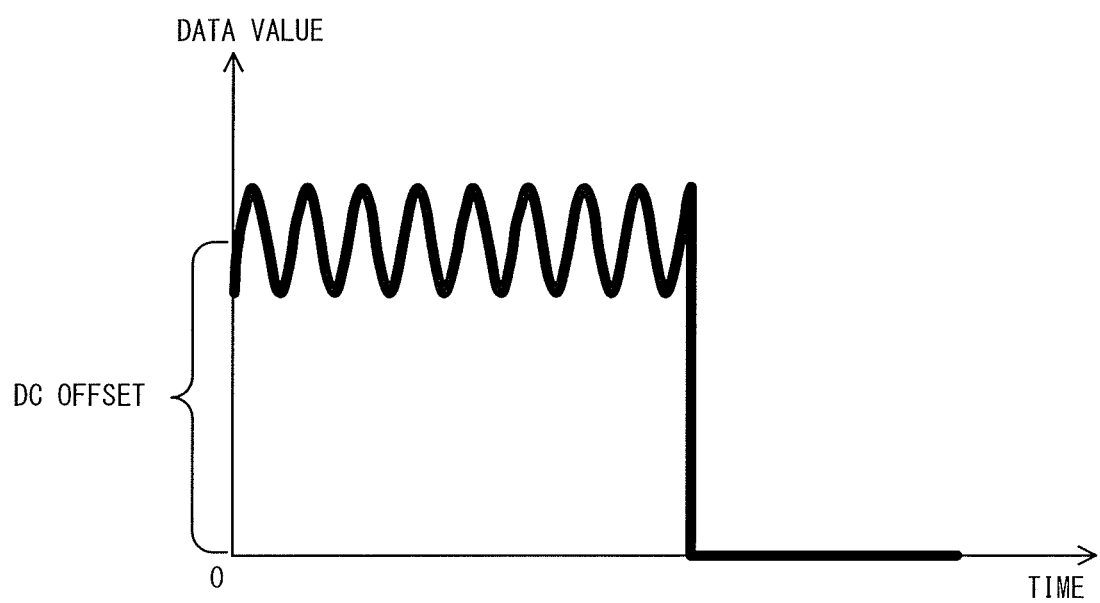
FIG. 5 is a graph schematically showing an example of a sequence of data supplemented with "0" data.
Figure 6:
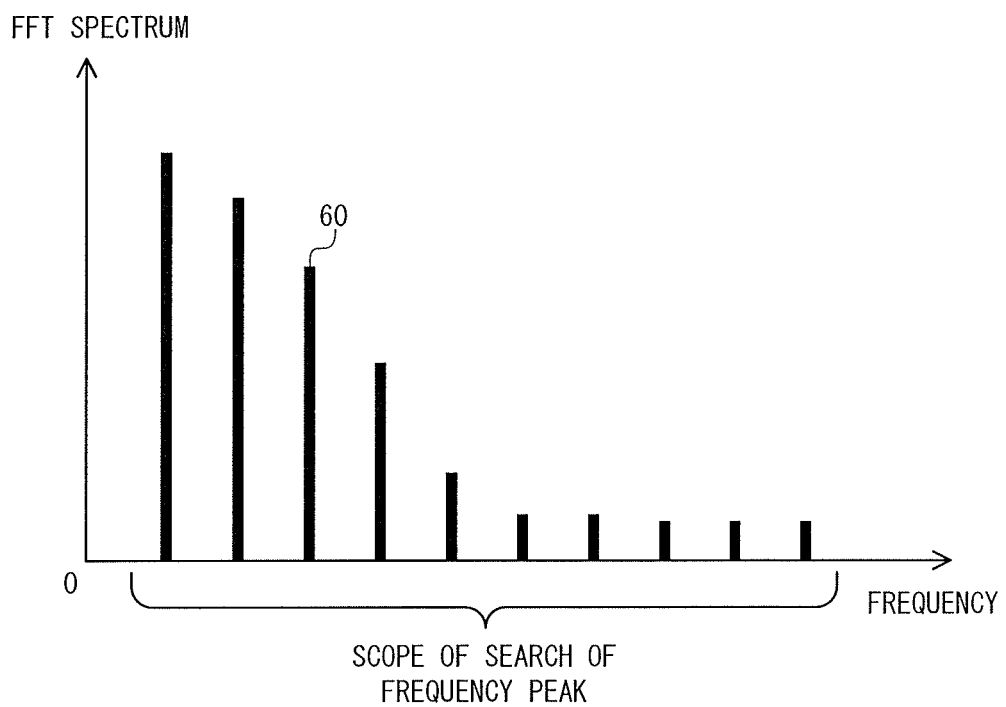
FIG. 6 is a graph schematically showing an example of frequency analysis results for the data sequence shown in FIG. 5.

Accordingly, the case where sampling data is supplemented with "0" data indicates that the data sequence as shown in FIG. 5 is generated. Thus, in the sampling data obtained by detecting light emitted to a part of a human body, it is unlikely in practice that "0" data indicates the center value of the signal associated with the pulse. When the FFT processing is performed on the data sequence as shown in FIG. 5, for example, in a frequency band lower than a frequency component 60 of the pulse to be originally acquired, a spectrum value larger than the frequency components of the pulse may be detected as shown in FIG. 6. This may lead to a failure in the measurement of the pulse rate.

As a countermeasure against this problem, it is possible to employ a method of eliminating the DC offset before execution of FFT processing, or a method of calculating the center value of the amplitude of the actual pulse signal. However, the signal components to be measured vary depending on how the device fits a part of the human body, the posture of the part of the human body, and the like during the measurement. For this reason, even when the center value is calculated and removed from the original signal and the signal is supplemented with "0" data, discontinuity occurs between the "0" data and the signal from which the center value is removed. Thus, the methods as mentioned above are impractical. Further, since the lower limit of the frequency of a pulse signal is about 0.5 Hz, a low-pass filter to eliminate signals having a frequency equal to or less than 0.5 Hz may be configured. However, the provision of such a low-pass filter results in an increase in processing time. When a power supply voltage is boosted, when a DC fluctuation occurs, or when a change occurs in an object to be measured, it takes a long time to stabilize the output of the filter, and it takes more time to perform the measurement.

Figure 7:
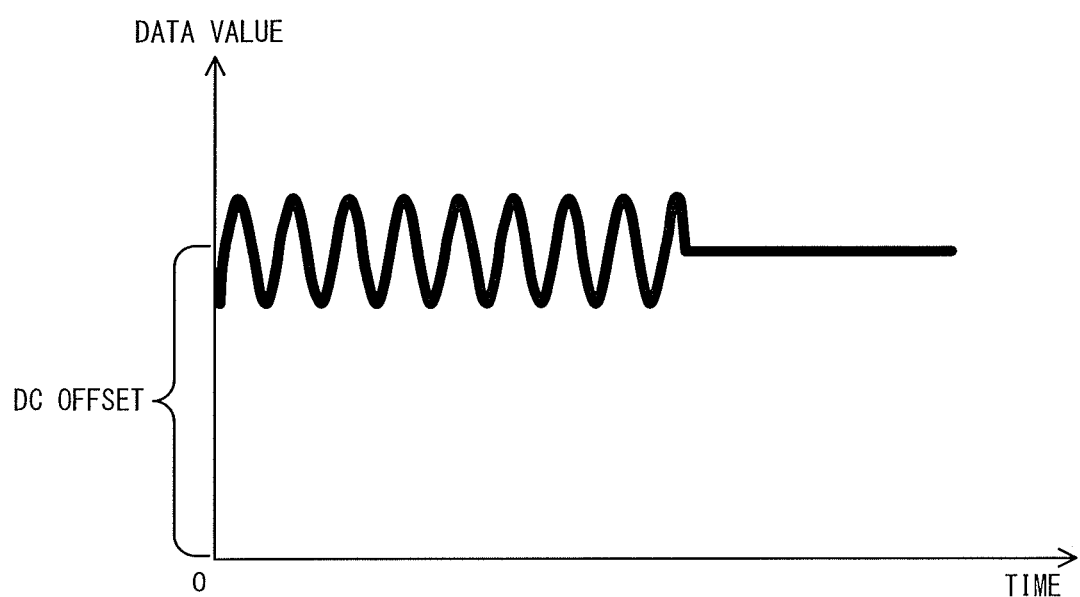
FIG. 7 is a graph schematically showing an example of a sequence of data supplemented with data replicated by a replication unit according to the first embodiment.
Figure 8:
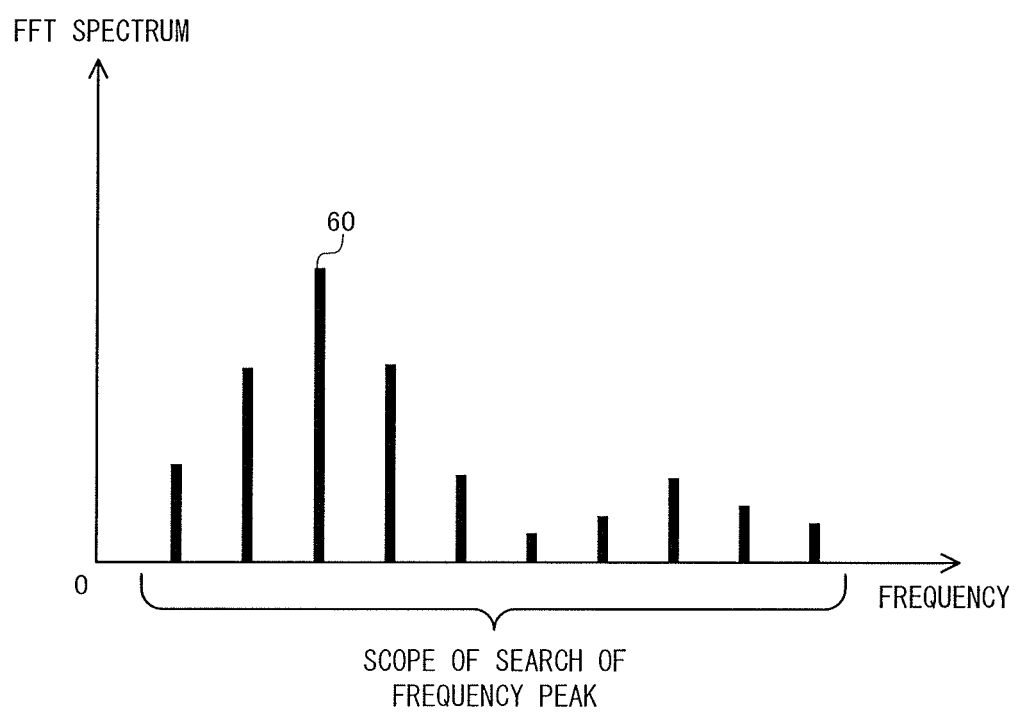
FIG. 8 is a graph schematically showing an example of frequency analysis results for the data sequence shown in FIG. 7.

On the other hand, in the pulsimeter 1 according to the first embodiment, in order to suppress the effect of the DC offset, the last one of the pieces of sampling data actually measured is replicated as shown in FIG. 7. Accordingly, the effect of the DC offset can be suppressed as shown in FIG. 8. Specifically, since the frequency components other than the frequency component 60 of the pulse to be originally acquired can be suppressed, the pulse can be calculated by extracting a frequency having a maximum spectrum value from the frequency analysis result. Further, since the frequency analysis is performed by securing the required sample number, deterioration in the resolution during the frequency analysis can be prevented and a reduction in the measurement range can be suppressed. Furthermore, the frequency analysis is performed without waiting until the number of pieces of actually measured sampling data reaches the required sample number, which leads to a reduction in the pulse measurement time. Note that the same advantageous effects can be obtained also when the final value is removed from the original signal after the data is supplemented with the final value of the actually measured sampling data, instead of supplementing the data with "0" data. On the other hand, in the case of removing the center value, discontinuity occurs as mentioned above, and thus the advantageous effects cannot be expected.

The replication unit 16, the frequency analysis unit 17, and the pulse rate calculation unit 18 are implemented by a microcomputer (microcontroller unit). More specifically, the microcomputer is composed of a CPU (Central Processing Unit), a non-volatile memory, and the like, and stores, in the non-volatile memory, programs respectively corresponding to the replication unit 16, the frequency analysis unit 17, and the pulse rate calculation unit 18. Each process is implemented by causing the CPU to execute the programs. The amplifier 13, the AD converter 14, and the buffer 15 may be incorporated in the microcomputer.

Second Embodiment

Next, a second embodiment will be described. The frequency analysis unit 17 according to the first embodiment performs the frequency analysis on the required sample number of pieces of data every time the first data number of pieces of sampling data are acquired. In the second embodiment, every time a predetermined third data number of pieces of data, which are less than the first data number of pieces of data, are acquired, second and subsequent frequency analyses are performed on the data sequence in which the first data number of pieces of latest sampling data including the third data number of pieces of sampling data are following by data obtained by replicating only the second data number of pieces of last obtained sampling data among the first data number of pieces of latest sampling data. Specifically, after n pieces of sampling data are acquired, when the pulse data acquisition unit 100 further acquires k (k is a positive integer, and k<n) pieces of sampling data, the replication unit 16 generates m pieces of sampling data using (k+1)-th to (n+k)-th sampling data and data obtained by replicating the (n+k)-th data, and the frequency analysis unit 17 performs the frequency analysis on m pieces of sampling data. The third data number may be changed according to an instruction from a user. Note that the components of the second embodiment are similar to the components of the first embodiment, except for the timing when the frequency analysis unit 17 performs the frequency analysis.

Figure 9:
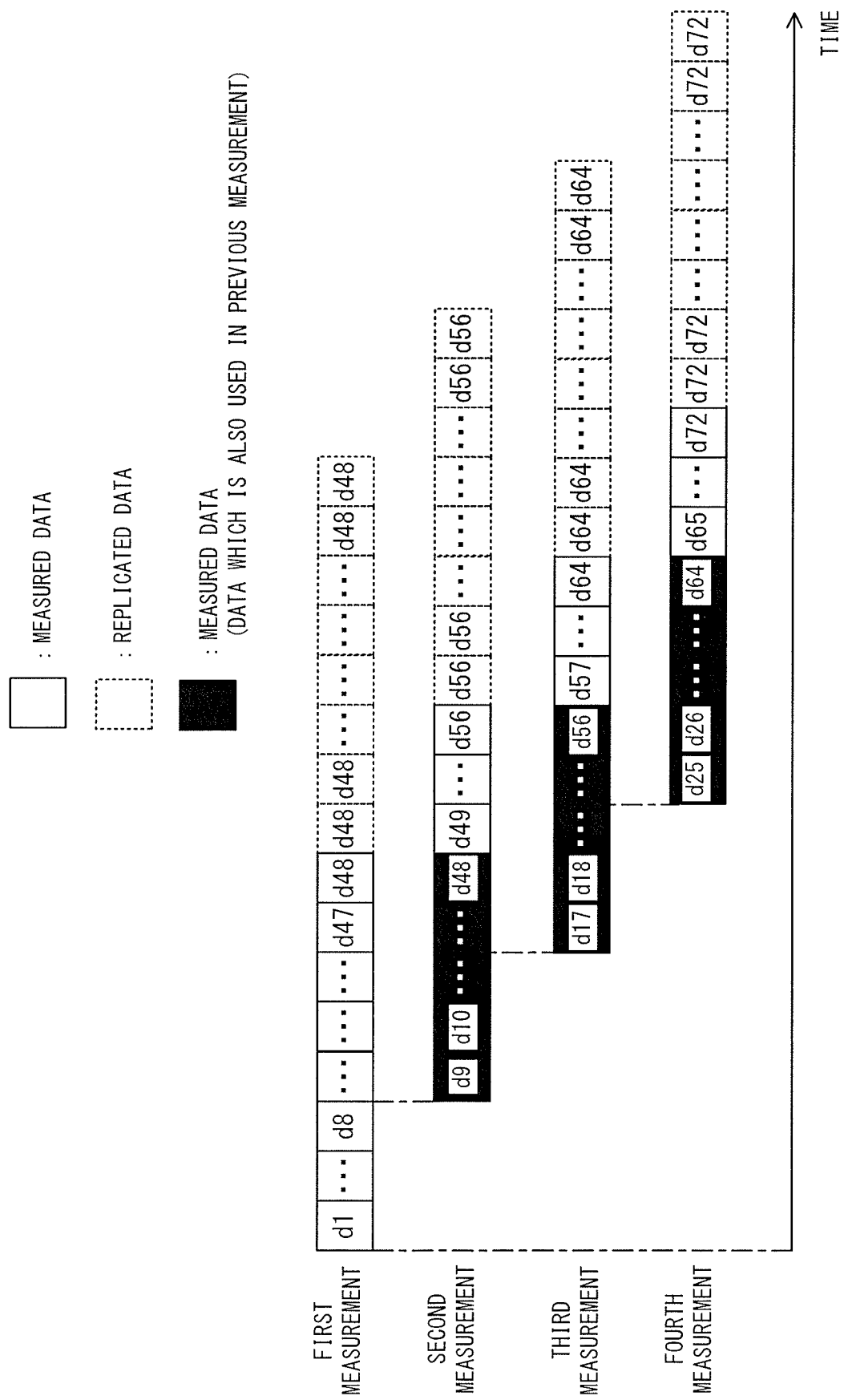
FIG. 9 is a schematic diagram illustrating a flow of operation of a pulsimeter according to a second embodiment.

The operation of the pulsimeter 1 according to the second embodiment will be described below with reference to FIG. 9. In an example shown in FIG. 9, assume that the required sample number is 128; the first data number indicating the number of pieces of actually measured sampling data is 48; the second data number indicating the number of pieces of replicated data supplemented to secure the required sample number is 80; and the third data number indicating the number of pieces of data corresponding to the interval at which the second and subsequent frequency analyses are performed is 8. Note that these numbers are merely examples and are not particularly limited. In FIG. 9, each rectangle indicated by a solid line represents actually measured sampling data and each rectangle indicated by a broken line represents replicated sampling data, as in the case shown in FIG. 4. A black rectangular area represents sampling data used for the frequency analysis during the previous pulse measurement.

In this specific example, the first pulse measurement is similar to that in the first embodiment shown in FIG. 4. Specifically, when the measurement is started and 48 pieces of sampling data are acquired, the first pulse rate measurement is carried out. However, in the example shown in FIG.

4, the second and subsequent pulse rate measurements are performed every time 48 pieces of sampling data are acquired, while in the example shown in FIG. 9, the measurements are performed every time eight pieces of sampling data are acquired.

More specifically, with a lapse of time from the start of the measurement, the sampling data d1, the sampling data d2, and . . . are sequentially accumulated in the buffer 15. When the 48th sampling data d48 counted from the start of the measurement is accumulated in the buffer 15, the replication unit 16 replicates 80 pieces of the sampling data d48. Upon completion of the replication, the replication unit 16 instructs the frequency analysis unit 17 to start the frequency analysis processing. Accordingly, the frequency analysis unit 17 performs the frequency analysis on 128 data sequences in which 48 data sequences from the sampling data d1 to the sampling data d48 are followed by 80 pieces of the sampling data d48. Thus, the result of the first pulse measurement is obtained.

After more time has passed since the start of the measurement, when the third data number of pieces of data, i.e., eight pieces of data, are further acquired, the replication unit 16 replicates the eighth data newly acquired. Specifically, when the 56th sampling data d56 counted from the start of the measurement is accumulated in the buffer 15, the replication unit 16 replicates 80 pieces of the sampling data d56. Further, the frequency analysis unit 17 performs the frequency analysis on 128 data sequences in which 48 data sequences from the sampling data d9 to the sampling data d56 that are the first data number of pieces of latest sampling data are followed by 80 pieces of the sampling data d56. Thus, the result of the second pulse measurement is obtained.

Next, when the 64th sampling data d64 counted from the start of the measurement is accumulated in the buffer 15, the replication unit 16 replicates 80 pieces of the sampling data d64. The frequency analysis unit 17 performs the frequency analysis on 128 data sequences in which 48 data sequences from the sampling data d17 to the sampling data d64 that are the first data number of pieces of latest sampling data are followed by 80 pieces of the sampling data d64. Thus, the result of the third pulse measurement is obtained.

Similarly, when the 72th sampling data d72 counted from the start of the measurement is stored in the buffer 15, the replication unit 16 replicates 80 pieces of the sampling data d72. The frequency analysis unit 17 performs the frequency analysis on 128 data sequences in which 48 data sequences from the sampling data d25 to the sampling data d72 that are the first data number of pieces of latest sampling data are followed by 80 pieces of the sampling data d72. Thus, the result of the fourth pulse measurement is obtained. After that, the measurement is performed in the same manner. Thus, the second and subsequent measurements are performed every time eight pieces of sampling data are acquired. That is, the measurement time can be reduced to one-sixth of the measurement time in the example shown in FIG. 4.

As described above, according to the pulsimeter 1 of the second embodiment, in the second and subsequent measurements, the measurement interval can be further shortened. Note that as shown in FIG. 9, the frequency analysis is performed using data sequences obtained by shifting the third data number of pieces of sampling data every time the measurement is performed. Accordingly, the buffer 15 is preferably configured as a ring buffer.

Third Embodiment

In the pulsimeter 1 according to the first and second embodiments described above, the pulse rate obtained in the first measurement is output only after the first data number of pieces of sampling data are accumulated. Accordingly, it takes a long time to obtain the output of the pulse rate in the first measurement. In order to solve this problem, a pulse measurement using a counter system is employed in combination with a pulse measurement using a frequency analysis in a third embodiment.

Figure 11:
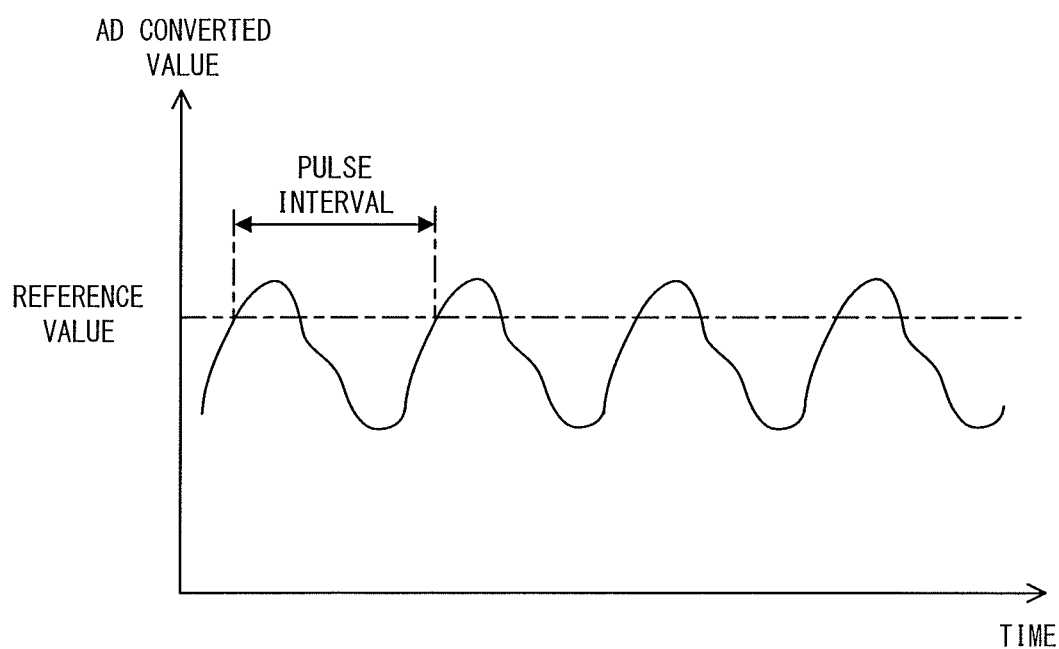
FIG. 11 is a graph schematically illustrating a pulse rate measurement using a counter system.

The term "pulse measurement using a counter system" described herein refers to a method of calculating a pulse rate by detecting a timing when a pulse waveform exceeds a reference value. FIG. 11 is a graph schematically illustrating the pulse measurement using the counter system. As shown in FIG. 11, in the pulse measurement using the counter system, each value of sampling data is monitored and a timing when the value exceeds a predetermined reference value is detected every time. Since a time interval between two adjacent timings corresponds to a pulse interval, the pulse rate per minute is calculated based on the time interval. The pulse measurement using the counter system has a feature that the measurement time is shorter than that in the pulse rate measurement using the FFT. Specifically, the pulse measurement using the counter system can be performed using sampling data corresponding to one pulse of a human, whereas the pulse rate measurement using the FFT requires sampling data corresponding to one or more pulses of a human. However, in the case of the pulse measurement using the counter system, it is necessary to appropriately set the reference value. Especially when the reflection optical sensor shown in FIG. 2 is used, the measurement environment is unstable due to, for example, variations in the position of an object to be measured, such as a finger, during the measurement, which makes it difficult to uniquely determine the reference value. Further, since it is necessary to perform sampling so that the pulse waveform can be reproduced in the pulse measurement using the counter system, it is preferable that the sampling period in the pulse measurement using the counter system be shorter in comparison to the pulse measurement using the FFT. Accordingly, there is a possibility that the LED lighting time increases, which leads to an increase in current consumption in the entire system. For this reason, in the third embodiment, the pulse measurement using the counter system is performed in a state where the data necessary for the frequency analysis is insufficient, and after the data necessary for the frequency analysis is accumulated, the measurement mode is switched to the pulse measurement using the frequency analysis.

Figure 10:
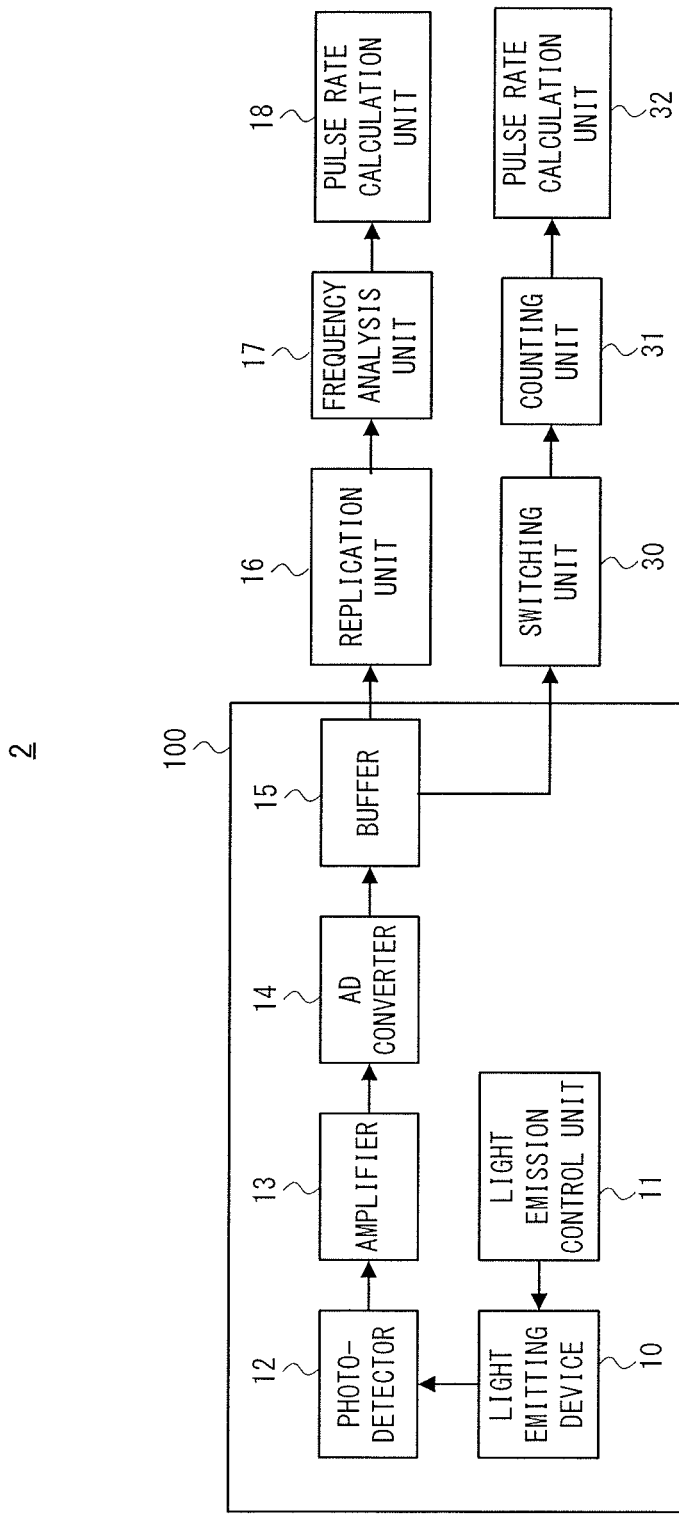
FIG. 10 is a block diagram showing a configuration of a pulsimeter according to a third embodiment.

FIG. 10 is a block diagram showing a configuration of a pulsimeter 2 according to the third embodiment. The pulsimeter 2 includes the pulse data acquisition unit 100, the replication unit 16, the frequency analysis unit 17, the pulse rate calculation unit 18, a switching unit 30, a counting unit 31, and a pulse rate calculation unit 32. That is, the pulsimeter 2 has a configuration in which the switching unit 30, the counting unit 31, and the pulse rate calculation unit 32 are added to the configuration of the pulsimeter 1. An explanation of the components of the pulsimeter 2 that are identical to those of the pulsimeter 1 will be omitted, and the additional components will be described.

The switching unit 30 switches the measurement mode between the pulse rate measurement using the frequency analysis and the pulse rate measurement using the counter system. Specifically, the switching unit 30 performs a control in such a manner that the pulse rate measurement using the counter system is executed until the number of pieces of acquired sampling data reaches the first data number, and after the number of pieces of acquired sampling data reaches the first data number, the pulse rate measurement using the frequency analysis is executed. The switching unit 30 may change the sampling period in the pulse rate measurement using the counter system from the sampling period in the pulse rate measurement using the frequency analysis. For example, the switching unit 30 may change the sampling period in such a manner that sampling data is acquired at a first sampling period until the number of pieces of acquired sampling data reaches the first data number, and after the number of acquired sampling data reaches the first data number, sampling data is acquired at a second sampling period which is longer than the first sampling period.

The counting unit 31 and the pulse rate calculation unit 32 are components that implement the pulse rate measurement using the counter system.

The counting unit 31 functions as a detection unit, and detects a timing when the value of each of the pieces of sampling data sequentially acquired exceeds a predetermined reference value. Every time the value of each of the pieces of sampling data exceeds the predetermined reference value, the counting unit 31 detects the timing when the value exceeds the predetermined reference value.

The pulse rate calculation unit 32 calculates the pulse rate based on the time interval between the timings detected by the counting unit 31. In accordance with the switching by the switching unit 30, the pulse rate calculation unit 32 measures the pulse rate until the first data number of pieces of sampling data are acquired.

Figure 12:
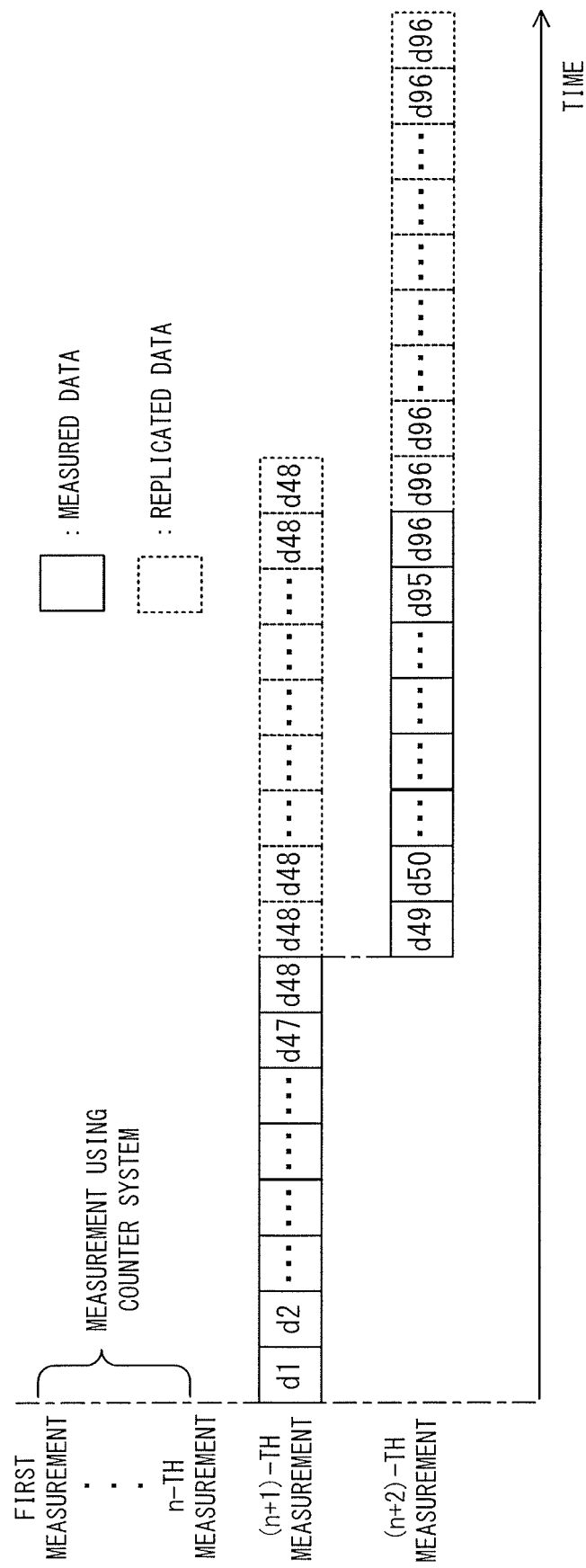
FIG. 12 is a schematic diagram illustrating a flow of operation of the pulsimeter according to the third embodiment.

The operation of the pulsimeter 2 will be described below with reference to FIG. 12. In the third embodiment, the method illustrated in the first embodiment as well as the method illustrated in the second embodiment can be applied to the pulse rate measurement using the frequency analysis. However, the third embodiment illustrates a case where the pulse rate measurement using the frequency analysis is performed by the method illustrated in the first embodiment. In an example shown in FIG. 12, assume that the required sample number is 128; the first data number indicating the number of pieces of actually measured sampling data is 48; and the second data number indicating the number of pieces of replicated data supplemented to secure the required sample number is 80, as in the case shown in FIG. 4. Note that these numbers are merely examples and are not particularly limited. In FIG. 12, each rectangle indicated by a solid line represents actually measured sampling data and each rectangle indicated by a broken line represents replicated sampling data, as in the case shown in FIG. 4.

In this specific example, the measurement using the counter system is repeated until 48 pieces of sampling data are acquired after the measurement is started, and after 48 pieces of sampling data are acquired, the pulse measurement using the frequency analysis is repeated. More specifically, the pulsimeter 2 operates in the following manner. First, with a lapse of time from the start of the measurement, the sampling data d1, the sampling data d2, and . . . are sequentially accumulated in the buffer 15. During a period from the start of the measurement to the time when the 48th sampling data d48 is accumulated in the buffer 15, the switching unit 30 selects the measurement by the counting unit 31 and the pulse rate calculation unit 32. Accordingly, during this time, the counting unit 31 monitors the sampling data sequentially acquired, and detects a timing when the value (AD converted value) of each of the pieces of sampling data changes from a value less than a reference value to a value equal to or greater than the reference value. The pulse rate calculation unit 32 calculates the pulse rate based on the time interval between two adjacent timings detected by the counting unit 31. The pulse rate measurement by the counting unit 31 and the pulse rate calculation unit 32 is repeated until 48 pieces of sampling data are acquired. In the example shown in FIG. 12, the pulse rate measurement by the counting unit 31 and the pulse rate calculation unit 32 is repeated n times. The pulse rate measurement by the counting unit 31 and the pulse rate calculation unit 32 may be performed every time counting is performed by the counting unit 31 in the manner as described above, or may be performed once. By performing the pulse measurement using the counter system as described above, the pulse rate can be measured prior to the acquisition of the first data number of pieces of data.

When the sampling data d48 is accumulated in the buffer 15, the switching unit 30 switches the measurement to the pulse measurement using the frequency analysis. The replication unit 16 replicates 80 pieces of the sampling data d48, and the frequency analysis unit 17 performs the frequency analysis on 128 data sequences in which 48 data sequences from the sampling data d1 to the sampling data d48 are followed by 80 pieces of the sampling data d48. The pulse rate calculation unit 18 calculates the pulse rate based on the obtained frequency analysis result. Thus, the (n+1)-th measurement is completed.

After more time has passed since the start of the measurement, when the 96th sampling data d96 counted from the start of the measurement is accumulated in the buffer 15, the replication unit 16 replicates 80 pieces of the sampling data d96. The frequency analysis unit 17 performs the frequency analysis on 128 data sequences in which 48 data sequences from the 49th sampling data d49 counted from the start of the measurement to the 96th sampling data d96 counted from the start of the measurement are followed by 80 pieces of the sampling data d96. The pulse rate calculation unit 18 calculates the pulse rate based on the obtained frequency analysis result. Thus, the (n+2)-th measurement is completed. After that, the pulse rate measurement based on the frequency analysis is repeated in the same manner every time the first data number of pieces (48 pieces in this example) of sampling data are acquired. As described above, in the example shown in FIG. 12, the frequency analysis is performed every time the first data number of pieces of sampling data are acquired. However, the frequency analysis maybe performed every time the third data number of pieces of sampling data are acquired.

As described above, according to the third embodiment, the pulse measurement using the counter system is performed until the first data number of pieces of sampling data are acquired. Accordingly, the pulse rate in the first measurement can be measured without waiting until the first data number of pieces of data are acquired.

The invention made by the present inventors has been described in detail by way of embodiments thereof. However, the present invention is not limited to the above embodiments, and can be modified in various ways without departing from the scope of the invention. For example, in the above embodiments, the configuration in which pulse data is acquired by the reflection sensor shown in FIG. 2 is employed. However, it is also possible to use a transmission sensor that emits light to a finger and receives the light, which has been transmitted through the finger, on a side opposite to a light emission side, to thereby acquire pulse data. Note that the object to be measured is not limited to a human body, but may be an animal. A part to be measured is not limited to a finger, but may be an arm, a palm, or a foot. The present invention may also be applied to a pulse measurement using a pulse oximeter. Further, the application of the present invention is not limited to the pulse measurement. The present invention can be used as a frequency analysis device to measure a periodic body motion, such as a walking cycle, and can also be used to detect a vibration of a structure or the like. The third embodiment illustrates the configuration in which the measurement mode is switched to the measurement using the counter system in the first measurement. However, not only in the first measurement, but also when a contingency, such as disturbance of data due to external factors, occurs during the measurement, the measurement mode may be switched to the measurement using the counter system.

The first to third embodiments can be combined as desirable by one of ordinary skill in the art.

While the invention has been described in terms of several embodiments, those skilled in the art will recognize that the invention can be practiced with various modifications within the spirit and scope of the appended claims and the invention is not limited to the examples described above.

Further, the scope of the claims is not limited by the embodiments described above.

Furthermore, it is noted that, Applicant's intent is to encompass equivalents of all claim elements, even if amended later during prosecution.

What is claimed is:

1. A pulsimeter comprising:
a processor programmed to:
sequentially acquire sampling data for a pulse rate calculation;
generate, when the number of pieces of acquired sampling data reaches n (n is a positive integer), m (m is a positive integer, and m>n) pieces of sampling data using the n pieces of sampling data and data obtained by multiple replicating n-th sampling data as last obtained sampling data in the n pieces;
perform a frequency analysis on the m pieces of sampling data; and
calculate a pulse rate based on a result of the frequency analysis.

2. The pulsimeter according to claim 1, wherein every time the processor acquires the n pieces of sampling data, the processor generates the m pieces of sampling data and the processor performs the frequency analysis on the m pieces of sampling data.

3. The pulsimeter according to claim 1, wherein when the processor further acquires k (k is a positive integer, and k<n) pieces of sampling data after the n pieces of sampling data are acquired, the processor generates the m pieces of sampling data using (k+1)-th to (n+k)-th sampling data and data obtained by replicating the (n+k)-th data, and the processor performs the frequency analysis on the m pieces of sampling data.

4. The pulsimeter according to claim 1, the processor is further programmed to:
detect a timing when a value of each of the pieces of data sequentially acquired by the processor exceeds a predetermined reference value; and
calculate a pulse rate based on a time interval of detected timings until the processor acquires the n pieces of sampling data.

5. The pulsimeter according to claim 1, further comprising:
a light emitting device that emits light to a blood vessel of an object to be measured;
a photodetector that detects light from the light emitting device through the blood vessel; and
a converter that performs an analog-to-digital conversion of a signal from the photodetector.

6. The pulsimeter according to claim 5, wherein the photodetector detects light from the light emitting device, the light being reflected from the blood vessel.

7. The pulsimeter according to claim 1, wherein the processor performs the frequency analysis by fast Fourier transform.

8. The pulsimeter according to claim 1, wherein n-th sampling data including DC offset signal is replicated while including the DC offset signal.

9. A frequency analysis device comprising:
a processor programmed to:
sequentially acquire sampling data;
generate, when the number of pieces of acquired sampling data reaches n (n is a positive integer), m (m is a positive integer, and m>n) pieces of sampling data using the n pieces of sampling data and data obtained by multiple replicating n-th sampling data as last obtained sampling data in the n pieces; and
perform a frequency analysis on the m pieces of sampling data.

10. The frequency analysis device according to claim 9, wherein n-th sampling data including DC offset signal is replicated while including the DC offset signal.

11. A pulse measurement method comprising:
sequentially acquiring sampling data for a pulse rate calculation;
generating, when the number of pieces of acquired sampling data reaches n (n is a positive integer), m (m is a positive integer, and m>n) pieces of sampling data using the n pieces of sampling data and data obtained by multiple replicating n-th sampling data as last obtained sampling data in the n pieces;
performing a frequency analysis on the m pieces of sampling data; and
calculating a pulse rate based on a result of the frequency analysis.

12. The pulse measurement method according to claim 11, wherein every time the n pieces of sampling data are acquired, the generating includes generating the in pieces of sampling data, and the performing includes performing the frequency analysis on the in pieces of sampling data.

13. The pulse measurement method according to claim 11, wherein when k (k is a positive integer, and k<n) pieces of sampling data are acquired after the n pieces of sampling data are acquired, the generating includes generating the m pieces of sampling data using (k+1)-th to (n+k)-th sampling data and data obtained by replicating the (n+k)-th data, and the performing includes performing the frequency analysis on the m pieces of sampling data.

14. The pulse measurement method according to claim 11, further comprising:
detecting a timing when a value of each of the pieces of sequentially obtained data exceeds a predetermined reference value; and
calculating a pulse rate based on a time interval of the timings detected until the n pieces of sampling data are acquired.

15. The pulse measurement method according to claim 11, wherein n-th sampling data including DC offset signal is replicated while including the DC offset signal.

* * * * *